United States Patent
Kopolow et al.

(10) Patent No.: US 6,939,934 B2
(45) Date of Patent: Sep. 6, 2005

(54) TERPOLYMER COMPOSITIONS FOR COATING SUBSTRATES USED IN COMPUTER PRINTERS

(75) Inventors: Stephen L. Kopolow, Plainsboro, NJ (US); David K. Hood, Basking Ridge, NJ (US); Drupesh Patel, Lake Hiawatha, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 10/926,519

(22) Filed: Aug. 26, 2004

(65) Prior Publication Data

US 2005/0027068 A1 Feb. 3, 2005

Related U.S. Application Data

(63) Continuation-in-part of application No. 10/388,697, filed on Mar. 14, 2003, and a continuation-in-part of application No. 10/153,411, filed on May 22, 2002, now Pat. No. 6,806,310.

(51) Int. Cl.$^7$ ................................................ C08F 26/08

(52) U.S. Cl. ..................... 526/264; 526/307; 526/307.5; 526/307.7; 526/320; 526/328.5; 524/555; 524/558; 524/560; 524/767; 524/808; 524/831; 524/833

(58) Field of Search ................................. 526/264, 307, 526/307.5, 307.7, 320, 328.5; 524/555, 558, 560, 767, 808, 831, 833

(56) References Cited

U.S. PATENT DOCUMENTS

| | | | |
|---|---|---|---|
| 6,225,429 B1 | * | 5/2001 | Chuang et al. ............. 526/264 |
| 6,361,768 B1 | * | 3/2002 | Galleguillos et al. .... 424/70.12 |
| 6,599,999 B1 | * | 7/2003 | Chandran et al. ........ 526/303.1 |
| 2003/0143180 A1 | * | 7/2003 | Giroud et al. |
| 2003/0219539 A1 | * | 11/2003 | Nigam |

* cited by examiner

*Primary Examiner*—Helen L. Pezzuto
(74) *Attorney, Agent, or Firm*—Walter Katz; William J. Davis

(57) ABSTRACT

Terpolymer compositions of vinyl caprolactam (VCL), dimethylaminopropyl methacrylamide (DMAPMA) and hydroxyethyl methacrylate (HEMA) are described to coat substrates for use in computer printers, and provide advantageous print quality thereon.

35 Claims, No Drawings

TERPOLYMER COMPOSITIONS FOR COATING SUBSTRATES USED IN COMPUTER PRINTERS

CROSS-REFERENCE TO RELATED U.S. PATENT APPLICATIONS

This application is a continuation-in-part of U.S. patent applications, Ser. No. 10/388,697, filed Mar. 14, 2003, and Ser. No. 10/153,411, filed May 22, 2002, now U.S. Pat. No. 6,806,310, both assigned to the same assignee as herein.

BACKGROUND OF THE INVENTION

1. Field of the Invention

This invention relates to polymer compositions used to coat substrates such as paper for use in computer printers, and, more particularly, to terpolymer compositions which provide advantageous light stability for dyes used in ink-jet printers.

2. Description of the Prior Art

The advent of color inkjet printing has been instrumental in fueling the print-on-demand revolution and has also created a number of challenges. Often, the surface of the desired media does not possess the necessary properties for accepting the ink-jet ink. This results in long dry times and/or a poor ink-jet image or light stability. It has long been recognized that a surface treatment or media coating plays a critical role in the final print quality. Numerous media coatings are known in the art. They may contain any number of components and often consist of more than one layer.

Accordingly, it is an object of this invention to provide a terpolymer composition which is particularly suitable for use in surface treating a substrate such as paper, polyester and vinyl plastics, canvas and the like, used in digital printing.

SUMMARY OF THE INVENTION

What is described herein is a terpolymer composition of vinyl caprolactam (VCL), dimethylaminopropyl methacrylamide (DMAPMA) and hydroxyethyl methacrylate (HEMA), uncrosslinked or crosslinked, unquaternized or quaternized, preferably crosslinked and quaternized, and a water or water/alcohol solution of the terpolymer, e.g. a water/alcohol solution of 20–40% solids of the terpolymer, preferably 25–35% solids of the terpolymer, having a viscosity of 3,000 to 25,000 cps (LV#4, 12 rpm, 25° C., 30% solids).

In other embodiments of the invention the terpolymer is present in the form of a powder.

Suitably, the terpolymer composition of the invention comprises, by wt., 60–90% VCL, 10–30% DMAPMA and 2–10% HEMA, preferably 75–80% VCL, 13–16% DMAPMA and 4–6% HEMA.

In other aspects of the invention, the terpolymer composition includes up to about 0.8% of a crosslinking agent, and up to 40% of a quaternizing agent.

Suitable crosslinking agents include pentaerythriol triallyl ether (PETE); pentaerythriol tetraacrylate (PETA).

Suitable quaternizing agents include HCl and $H_2SO_4$.

Preferably the crosslinking agent is present in an amount of 0.5–0.7%; and the quaternizing agent in an amount of 2.5–3.5%, by wt. of the terpolymer.

The invention therein includes a process of making the terpolymer composition described above which comprises the steps of polymerizing the monomers in an aqueous-alcohol solvent, suitably wherein the alcohol is ethanol or isopropyl alcohol, at about 20–40% solids, in the presence or absence of a crosslinking agent, thereafter, if desired, quaternizing the product, removing the alcohol solvent to provide a water only solution of the terpolymer, and drying to provide the terpolymer in the form of a powder.

The invention also includes use formulations of the terpolymer of the invention, optionally with other water/alcohol-born ingredients, e.g. polyvinyl alcohol (PVA), latex, acrylate polymers, styrene-butadiene latex, crosslinkers, gelatin or a cellulosic ingredient.

The terpolymer may be post-treated, if desired, e.g. by heating with a post-treating crosslinking agent, to increase its viscosity or enhance the water resistance of the dried film, as described in detail in the aforementioned U.S. patent applications. Suitable post-treatment crosslinkers described therein include polyepoxides, e.g. Ancarez AR 550; melamine/formaldehyde resins, e.g. Berset 2003; and aziridines.

In commercial use for digital inkjet printing, a suitable substrate such as paper, polyester or vinyl plastics, canvas and the like, is coated with he terpolymer of the invention to render the coated substrate more receptive to inkjet printing. Such coated substrates exhibit particularly advantageous light stability to dyes ordinarily present in inkjet-printers.

The invention will be described in more detail by reference to the following examples in which:

EXAMPLE 1

VCL/DMAPMA/HEMA/PETE/HCL in Water/ETOH

1. Set up 1.0 l autoclave reactor fitted with anchor type agitator, thermocouple and nitrogen purging line.
2. Charge the reactor initially with 79.83 g of DI water, 22.50 g of ethanol SDA-40B, 240.00 g of 50/50 mixture of vinyl caprolactam and ethanol, 0.9240 g of PETE.
3. Pressurize the reaction mixture with nitrogen for 3 times at 60 psig and hold it for 2 minutes and release it, leave the pressure to about 10 psig during reaction.
4. Heat it to 80° C., during which take 22.50 g of DMAPMA, 7.50 g of HEMA mixed with 107.5 g of DI water and purge it with nitrogen for 15 minutes and then charge to the pump.
5. At 80° C., charge 26.99 ml of DMAPMA/HEMA/water mixture by using pump in 5 minutes.
6. Then set time=0 minutes, add first shot of Vazo-67 by mixing 0.3542 g of Vazo-67 with 1.2500 g of ethanol SDA 40B, and also start continuous addition of DMAPMA/water for 360 minutes at the flow rate of 0.310 ml/min.
7. Add another shots of Vazo-67 by mixing 0.3542 g of Vazo-67 with 1.2500 g of ethanol SDA 40B at 60, 180, 300, 420, 600 and 840 minutes. [Total 7 shots of Vazo-67].
8. Hold the reaction for two more hours after final shot of Vazo-67 and check residual VCL at 960 minutes, if VCL is higher than 2000 ppm then add one more shots of Vazo-67 and hold for two more hours or else, cool down the reaction to 40° C.
9. Then neutralize the batch with conc. HCl. The final pH should be in the range of 6.5 to 7.5.
10. Filter it through Millipore filter tube using 41μ screen.

EXAMPLE 2

VCL/DMAPMA/HEMA/HCL in Water/ETOH

1. Set up 10 l autoclave reactor fitted with anchor type agitator, thermocouple and nitrogen purging line.

2. Charge the reactor initially with 79.83 g of DI water, 22.50 g of ethanol SDA-40B, 240.00 g of 50/50 mixture of vinyl caprolactam and ethanol.
3. Pressurize the reaction mixture with nitrogen for 3 times at 60 psig and hold it for 2 minutes and release it, leave the pressure to about 10 psig during reaction.
4. Heat it to 80° C., during which take 22.50 g of DMAPMA, 7.50 g of HEMA mixed with 107.5 g of DI water and purge it with nitrogen for 15 minutes and then charge to the pump.
5. At 80° C., charge 26.99 ml of DMAPMA/HEMA/water mixture by using pump in 5 minutes.
6. Then set time=0 minutes, add first shot of Vazo-67 by mixing 0.3542 g of Vazo-67 with 1.2500 g of ethanol SDA 40B, and also start continuous addition of DMAPMA/water for 360 minutes at the flow rate of 0.310 ml/min.
7. Add another shots of Vazo-67 by mixing 0.3542 g of Vazo-67 with 1.2500 g of ethanol SDA 40B at 60, 180, 300, 420, 600 and 840 minutes. [Total 7 shots of Vazo-67].
8. Hold the reaction for two more hours after final shot of Vazo-67 and check residual VCL at 960 minutes, if VCL is higher than 2000 ppm then add one more shots of Vazo-67 and hold for two more hours or else, cool down the reaction to 40° C.
9. Then neutralize the batch with conc. HCl. The final pH should be in the range of 6.5 to 7.5.
10. Filter it through Millipore filter tube using 41$\mu$ screen.

EXAMPLE 3

VCL/DMAPMA/HEMA/PETE/HCL in Water

1. Set up 1.0 l autoclave reactor fitted with anchor type agitator, thermocouple and nitrogen purging line.
2. Charge the reactor initially with 79.83 g of DI water, 22.50 g of ethanol SDA-40B, 240.00 g of 50/50 mixture of vinyl caprolactam and ethanol, 0.9240 g of PETE.
3. Pressurize the reaction mixture with nitrogen for 3 times at 60 psig and hold it for 2 minutes and release it, leave the pressure to about 10 psig during reaction.
4. Heat it to 80° C., during which take 22.50 g of DMAPMA, 7.50 g of HEMA mixed with 107.5 g of DI water and purge it with nitrogen for 15 minutes and then charge to the pump.
5. At 80° C., charge 26.99 ml of DMAPMA/HEMA/water mixture by using pump in 5 minutes.
6. Then set time=0 minutes, add first shot of Vazo-67 by mixing 0.3542 g of Vazo-67 with 1.2500 g of ethanol SDA 40B, and also start continuous addition of DMAPMA/water for 360 minutes at the flow rate of 0.310 ml/min.
7. Add another shots of Vazo-67 by mixing 0.3542 g of Vazo-67 with 1.2500 g of ethanol SDA 40B at 60, 180, 300, 360, 480, 600 and 840 minutes. [Total 7 shots of Vazo-67].
8. Hold the reaction for two more hours after final shot of Vazo-67 and check residual VCL at 960 minutes, if VCL is higher than 2000 ppm then add one more shots of Vazo-67 and hold for two more hours or else, cool down the reaction to 40° C.
9. Then neutralize the batch with conc. HCl. The final pH should be in the range of 6.5 to 7.5.
10. Distill off ethanol to replace with DI water using vacuum. % Ethanol should be less than 5.0%, and adjust the final % solids to 30%.
11. Add 0.85 g [0.17% of batch size of 500 g] of BTC-50NF as preservative. Stir for 1.0 hour.
12. Filter it through Millipore filter tube using 41$\mu$ screen.

EXAMPLE 4

VCL/DMAPMA/HEMA/HCL in Water

1. Set up 1.0 l autoclave reactor fitted with anchor type agitator, thermocouple and nitrogen purging line.
2. Charge the reactor initially with 79.83 g of DI water, 22.50 g of ethanol SDA-40B, 240.00 g of 50/50 mixture of vinyl caprolactam and ethanol.
3. Pressurize the reaction mixture with nitrogen for 3 times at 60 psig and hold it for 2 minutes and release it, leave the pressure to about 10 psig during reaction.
4. Heat it to 80° C., during which take 22.50 g of DMAPMA, 7.50 g of HEMA mixed with 107.5 g of DI water and purge it with nitrogen for 15 minutes and then charge to the pump.
5. At 80° C., charge 26.99 ml of DMAPMA/HEMA/water mixture by using pump in 5 minutes.
6. Then set time=0 minutes, add first shot of Vazo-67 by mixing 0.3542 g of Vazo-67 with 1.2500 g of ethanol SDA 40B, and also start continuous addition of DMAPMA/water for 360 minutes at the flow rate of 0.310 ml/min.
7. Add another shots of Vazo-67 by mixing 0.3542 g of Vazo-67 with 1.2500 g of ethanol SDA 40B at 60, 180, 300, 360, 480, 600 and 840 minutes. [Total 7 shots of Vazo-67].
8. Hold the reaction for two more hours after final shot of Vazo-67 and check residual VCL at 960 minutes, if VCL is higher than 2000 ppm then add one more shots of Vazo-67 and hold for two more hours or else, cool down the reaction to 40° C.
9. Then neutralize the batch with conc. HCl. The final pH should be in the range of 6.5 to 7.5.
10. Distill off ethanol to replace with DI water using vacuum. % Ethanol should be less than 5.0%, and adjust the final % solids to 30%.
11. Add 0.85 g [0.17% of batch size of 500 g] of BTC-50NF as preservative. Stir for 1.0 hour.
12. Filter it through Millipore filter tube using 41$\mu$ screen.

EXAMPLE 5

Dye Color Stability for Composition

Test Pattern

The light fastness of the polymer was measured by applying a 10% solids solution to polyester film using a #38 Meyer bar (film thickness ~9 micron). The film was then dried in oven and then a test pattern was printed using a HP 832C ink jet color printer.

Light Fastness (Color Stability to UV Light)

The test strip from the test pattern print was subjected to UV light for 24 hours using an Atlas sun tester (ASTM G 53–84 test method). The optical density (using a Macbeth Densitometer) of the four colors are measured on the control and the treated strips and the percent fading is reported. Percent fading is the optical density of the color on the untreated strip minus the optical density of the color on the treated strip divided by the optical density of the color on the untreated strip.

For PVP containing polymers (copolymers) the percent fading was above 50%, whereas, for the VCL polymers (terpolymers) the percent fading was less than 25%.

EXAMPLE 6

Powders of Terpolymer Compositions of Invention

The aqueous terpolymer compositions of Examples 3 and 4 were dried using a drum dryer, a freeze dryer, a belt dryer, or by spray drying, to provide the terpolymer composition in the form of a powder.

EXAMPLE 7

Inkjet Printable Coating # 1
1. Add 294 g of water to a 1-L beaker. Adjust pH to 9–10 with sodium hydroxide (Aldrich).
2. Add 20.9 g of barium sulfate (Aldrich).
3. Add 20.9 g of Engelhard Disintex 1000.
4. Add 20.9 g of Millennium Chemicals Silcron G100 silica. Homogenize and mix thoroughly.
5. Add 10 g of Dow UCAR Latex 313 while mixing.
6. Add 53 g of VCL/DMAPMA/HEMA/PETE/HCl (30% solids) while mixing.
7. Add 9 g of Air Products Ancarez AR 550. Homogenize and mix thoroughly.

Coat on substrate such as polyester, canvas or paper with #40 Meyer rod, and dry in air oven at 135° C. Print on HP 880C in Premium Photo Paper Mode. Improved light stable, water resistive prints are achieved.

EXAMPLE 8

Inkjet Printable Coating #2
1. Add 56.9 g of water to 200 mL beaker.
2. Add 39 g of ISP/PCI Aquazol 200 (9.2% solids).
3. Add 17 g of VCL/DMAPMA/HEMA/PETE/HCl (30% solids).
4. Add 0.1 g of ISP Easy Sperse.
5. Add 0.2 g of Eastman CP 349W.
6. Add 1 g of concentrated ammonium hydroxide. Continue to adjust pH until pH~9 to 10.
7. Add 0.3 g Bayer XAMA-7.

Coat on substrate such as polyester, vinyl or paper with #40 Meyer rod, and dry in air oven. Print on HP 880C in Premium Photo Paper Mode. Light stable prints are achieved.

EXAMPLE 9

Inkjet Printable Coating #3
1. Add 40 g of water to 200 mL beaker.
2. Add 20 g of Aldrich 88% hydrolyzed polyvinyl alcohol (20% solids).
3. Add 22 g of VCL/DMAPMA/HEMA/PETE/HCl (30% solids).
4. Add 0.3 g of Cytec Cycat 4040.
5. Add 0.2 g of Bercen Berset 2003.

Coat on substrate such as polyester or paper with #40 Meyer rod, and dry in air oven at 135° C. Print on HP 880C in Premium Photo Paper Mode. Light stable prints are achieved.

EXAMPLE 10

The VCL/DMAPMA/HEMA/PETE/HCl terpolymer are used in conjunction with acrylic polymers, acrylic copolymers, alginates, cross-linkers, carrageenan, microcrystalline cellulose, gelatin, carboxymethylcellulose sodium, hydroxyethylcellulose, hydroxypropylcellulose, hydroxypropylmethylcellulose, methylcellulose, guar and guar derivatives, locust bean gum, organoclays, polyethylene oxide, polyvinylpyrrolidones, copolymers of polyvinylpyrrolidones, silica, aluminates, zirconates, calcium carbonate, water-swellable clay, xanthan gum and pigments (inorganic) to achieve advantageous inkjet printable surface coatings having light stability.

While the invention has been described with particular reference to certain embodiments thereof, it will be understood that changes and modifications may be made which are within the skill of the art. Accordingly, it is intended to be bound only by the following claims, in which:

What is claimed is:
1. A terpolymer composition consisting essentially of vinyl caprolactam (VCL), dimethylaminopropyl methacrylamide (DMAPMA) and hydroxyethyl methacrylate (HEMA), uncrosslinked or crosslinked, unquaternized or quaternized, which exhibits light stability to dyes found in ink-jet printers, as evidenced by a less than 25% color fading in the ASTM G-53-84 test.
2. A terpolymer according to claim 1 which is uncrosslinked.
3. A terpolymer according to claim 1 which is crosslinked.
4. A terpolymer according to claim 1 which is unquaternized.
5. A terpolymer according to claim 1 which is quaternized.
6. A terpolymer according to claim 1 which is crosslinked and quaternized.
7. A water/alcohol solution of the terpolymer of claim 1.
8. A water/alcohol solution of the terpolymer of claim 6.
9. A water solution of the terpolymer of claim 1.
10. A water solution of the terpolymer of claim 6.
11. A water/alcohol solution of 20–40% solids of the terpolymer of claim 1.
12. A water/alcohol solution of 25–35% solids of the terpolymer of claim 1.
13. A water/alcohol solution containing 20–40% solids of the terpolymer of claim 6.
14. A water/alcohol solution containing 25–35% solids of the terpolymer of claim 6.
15. A water/alcohol solution of claim 1 having a viscosity of 3,000 to 25,000 cps (LV#4, 12 rpm, 25° C., 30% solids).
16. A terpolymer according to claim 1 which is in the form of a powder.
17. A terpolymer according to claim 6 which is in the form of a powder.
18. A terpolymer composition according to claim 1 comprising, by wt., 60–90% VCL, 10–30% DMAPMA and 2–10% HEMA.
19. A terpolymer composition according to claim 18 comprising 75–80% VCL, 13–16% DMAPMA and 4–6% HEMA.
20. A terpolymer composition according to claim 18 including up to about 0.8% of a crosslinking agent.
21. A terpolymer composition according to claim 18 including up to 40% of a quaternizing agent.
22. A terpolymer composition according to claim 18 in which the crosslinking agent is pentaerythriol triallyl ether (PETE).
23. A terpolymer according to claim 18 in which the quaternizing agent is HCl.
24. A terpolymer according to claim 18 in which the crosslinking agent is present in an amount of 0.5–0.7% by wt. of the terpolymer.
25. A terpolymer according to claim 21 in which quaternizing agent is present in an amount of 2.5–3.5% by wt. of the terpolymer.
26. A process of making the terpolymer composition of claim 1 which comprises polymerizing the monomers in an aqueous-alcohol solvent.
27. A process according to claim 21 wherein said alcohol is ethanol or isopropyl alcohol.
28. A process according to claim 26 which is carried out at 20–40% solids.

29. A process according to claim 26 which is carried out in the presence of a crosslinking agent.

30. A process according to claim 26 which is carried out in the absence of a crosslinking agent.

31. A process according to claim 26 in which the product is thereafter quaternized.

32. A process according to claim 26 including the additional step of removing the alcohol solvent to provide a water solution of the terpolymer.

33. A process according to claim 31 in which the water solution is dried to provide the terpolymer in the form of a powder.

34. A terpolymer according to claim 1 which is post-treated and crosslinked.

35. A terpolymer according to claim 1 which is post-treated with a polyepoxide, melamine/formaldehyde resin, or aziridine crosslinker.

* * * * *